(12) United States Patent
Sakai et al.

(10) Patent No.: US 11,371,015 B2
(45) Date of Patent: Jun. 28, 2022

(54) GRAFT POLYMER, TEMPERATURE-RESPONSIVE SUBSTRATE FOR CELL CULTURE USING THE SAME AND PRODUCTION METHOD THEREFOR, AS WELL AS LIQUID CHROMATOGRAPHIC CARRIER HAVING THE NOVEL GRAFT POLYMER IMMOMIBILIZED THEREON AND LIQUID CHROMATOGRAPHIC METHOD USING THE SAME

(71) Applicant: Hideaki Sakai, Kawasaki (JP)

(72) Inventors: Hideaki Sakai, Kawasaki (JP); Masa-aki Kakimoto, Yokohama (JP); Yu Sudo, Tokyo (JP)

(73) Assignee: Hideaki Sakai, Kawasaki (JP)

( * ) Notice: Subject to any disclaimer, the term of this patent is extended or adjusted under 35 U.S.C. 154(b) by 0 days.

(21) Appl. No.: 17/184,310

(22) Filed: Feb. 24, 2021

(65) Prior Publication Data

US 2021/0180011 A1    Jun. 17, 2021

Related U.S. Application Data

(63) Continuation of application No. 16/660,897, filed on Oct. 23, 2019, now abandoned, which is a
(Continued)

(30) Foreign Application Priority Data

| Feb. 28, 2013 | (JP) | ................................ | 2013-055630 |
| Feb. 28, 2013 | (JP) | ................................ | 2013-055631 |
| Aug. 27, 2013 | (JP) | ................................ | 2013-189831 |

(51) Int. Cl.
*C12N 5/00* (2006.01)
*B01J 20/26* (2006.01)
(Continued)

(52) U.S. Cl.
CPC ....... *C12N 5/0068* (2013.01); *B01D 15/3876* (2013.01); *B01J 20/264* (2013.01);
(Continued)

(58) Field of Classification Search
CPC ........................... C08F 257/02; C12N 5/0068
See application file for complete search history.

(56) References Cited

U.S. PATENT DOCUMENTS

| 5,284,766 A | 2/1994 | Okano et al. |
| 2007/0092492 A1 | 4/2007 | Matsuda et al. |

(Continued)

FOREIGN PATENT DOCUMENTS

| JP | 61-283345 | 12/1986 |
| JP | 2-211865 | 8/1990 |

(Continued)

OTHER PUBLICATIONS

Extended European Search Report issued in App. No. 14756615.2 dated Jan. 9, 2017.
(Continued)

*Primary Examiner* — Mark S Kaucher
(74) *Attorney, Agent, or Firm* — Nixon & Vanderhye P.C.

(57) ABSTRACT

By using a graft polymer comprising a dendritic polymer with a styrene skeleton and a hydrophilic polymer grafted to a terminal thereof, a temperature-responsive substrate for cell culture having a temperature-responsive surface for cell culture that allows cells to be cultured with high efficiency and which yet allows cultured cells to be exfoliated in a short period of time and with high efficiency by simply changing the temperature of the substrate surface can be prepared conveniently. If this temperature-responsive substrate for cell culture is used, cells obtained from a variety of tissues can be cultured with high efficiency. If this culture method is utilized, cultured cells can be exfoliated intact in a short (Continued)

amount of time with high efficiency. In addition, by using this graft polymer, a wide range of peptides and proteins can also be separated by simply changing the temperature of a chromatographic carrier. This allows for convenient separation procedure and improves the efficiency of separating operations. What is more, the stereoregularity of the dendritic polymer per se may be utilized to enable separation of solutes based on differences in their molecular structures.

6 Claims, 7 Drawing Sheets

Related U.S. Application Data continuation of application No. 16/208,163, filed on Dec. 3, 2018, now abandoned, which is a continuation of application No. 14/771,068, filed as application No. PCT/JP2014/055178 on Feb. 28, 2014, now abandoned.

(51) Int. Cl.

| | | |
|---|---|---|
| *B01J 20/286* | (2006.01) | |
| *B01J 20/32* | (2006.01) | |
| *B01D 15/38* | (2006.01) | |
| *C12M 1/00* | (2006.01) | |
| *C08F 299/00* | (2006.01) | |
| *C08F 293/00* | (2006.01) | |
| *C08F 257/02* | (2006.01) | |
| *C08L 51/00* | (2006.01) | |
| *C08L 101/04* | (2006.01) | |
| *B01D 15/30* | (2006.01) | |
| *B01D 15/32* | (2006.01) | |

(52) U.S. Cl.
CPC .......... *B01J 20/286* (2013.01); *B01J 20/321* (2013.01); *B01J 20/3278* (2013.01); *C08F 257/02* (2013.01); *C08F 293/005* (2013.01); *C08F 299/00* (2013.01); *C08L 51/003* (2013.01); *C08L 101/04* (2013.01); *C12M 23/20* (2013.01); *B01D 15/305* (2013.01); *B01D 15/327* (2013.01); *C08F 2438/03* (2013.01); *C08L 2203/02* (2013.01); *C12N 2533/30* (2013.01); *C12N 2539/10* (2013.01)

(56) References Cited

U.S. PATENT DOCUMENTS

| | | |
|---|---|---|
| 2009/0238889 A1 | 9/2009 | Weide et al. |
| 2010/0120984 A1 | 5/2010 | Ozawa et al. |
| 2011/0117668 A1 | 5/2011 | Stayton |
| 2013/0309927 A1 | 11/2013 | Jangbarwala |
| 2014/0212973 A1 | 7/2014 | Nakayama et al. |
| 2015/0337128 A1 | 11/2015 | Gray et al. |

FOREIGN PATENT DOCUMENTS

| | | |
|---|---|---|
| JP | 5-133947 | 5/1993 |
| JP | 5-192138 | 8/1993 |
| JP | 7-318661 | 12/1995 |
| JP | 2004-124051 | 4/2004 |
| JP | 2005-8802 | 1/2005 |
| JP | 2005-292104 | 10/2005 |
| JP | 2007-528755 | 10/2007 |
| JP | 2008-220354 | 9/2008 |
| JP | 2010-505015 | 2/2010 |
| JP | 2013-59312 | 4/2013 |
| JP | 2015-519902 | 7/2015 |
| WO | WO 2008/133283 | 11/2008 |
| WO | WO 2012/029882 | 3/2012 |

OTHER PUBLICATIONS

He et al., "Solvent Replacement to Thermo-Responsive Nanoparticles from Long-Subchain Hyperbranched PSt Grafted with PNIPAM for Encapsulation," *Journal of Polymer Science Part A: Polymer Chemistry*, vol. 51: 2142-2149 (2013).

International Search Report issued in App. No. PCT/JP2014/055178 dated Jun. 10, 2014.

Japanese Office Action issued in Appln. No. 2015-503068 dated Apr. 10, 2018 (w/ translation).

Kee et al. "Arborescent Polystyrene-graft-Poly(tert-Butyl Methacrylate) Copolymers: Synthesis and Enhanced Polyelectrolyte Effect in Solution," *Journal of Polymer Science: Part A: Polymer Chemistry*, vol. 46: 2335-2346 (2009).

Loh et al. "Novel poly(N-isopropylacrylamide)-poly[(R)-3-hydroxybutyrate]-poly(N-isopropylacrylamide) triblock copolymer surface as a culture substrate for human mesenchymal stem cells," *Soft Matter*, vol. 5, pp. 2937-2946 (2009), The Royal Society of Chemistry.

Mittal et al., "Macromolecular Nanotechnology: Synthesis of temperature responsive polymer brushes form polystyrene latex particles functionalized with ATRP initiator," *European Polymer Journal*, vol. 43: 4868-4881 (2007).

Moran et al., "Intact endothelial cell sheet harvesting from thermoresponsive surfaces coated with cell adhesion promoters," *J. R. Soc. Interface*, vol. 4, 1151-1157 (2007), The Royal Society.

Njikang et al., "Pressure- and Temperature-Induced Association of Arborescent Polystyrene-graft-poly(ethylene oxide) Copolymers at the Air-Water Interface," *Langmuir*, vol. 24, No. 22: 12919-12927 (2008).

Partial Supplementary European Search Report issued in App. No. 14756615.2 dated Oct. 7, 2016.

Vogt et al., "Hyperbranched Polymers via RAFT Copolymerization of an Acryloyl Trithiocarbonate" *Australian Journal of Chemistry* 2007, 60, 396-399.

Zhao et al., "Inhibition of Electrochemical Reactions at Gold Surfaces by Grafted, Highly Fluorinated, Hyperbranched Ploymer Films" *Langmuir*, vol. 13, No. 6: 1388-1391 (1997).

Office Action issued in JP Appln. No. 2019-023465 dated Mar. 17, 2020 (w/ translation).

Office Action issued in JP Appln. No. 2019-023465 dated Mar. 17, 2020.

Figure 1
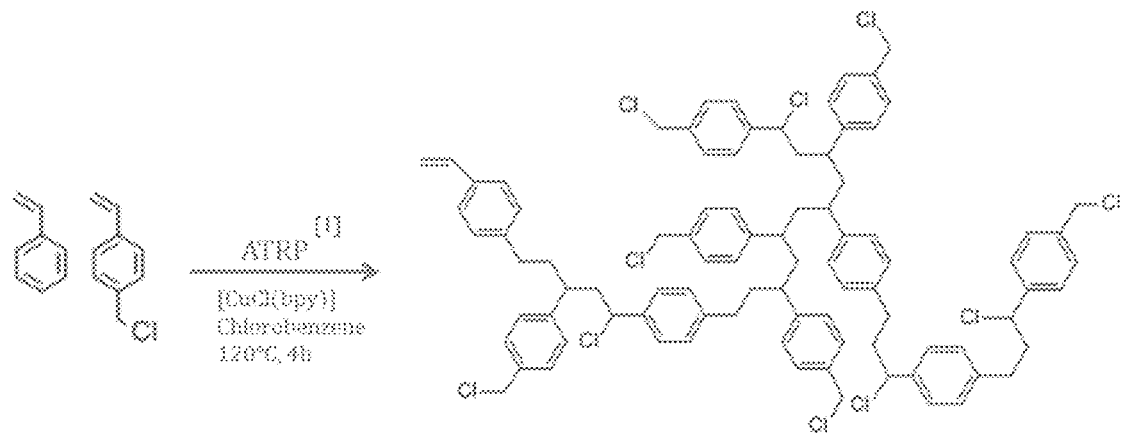
Figure 2
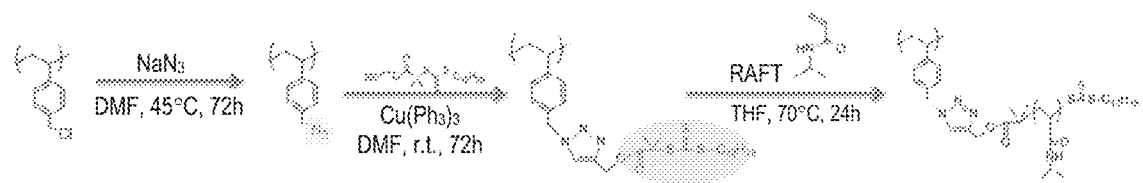
Figure 3
| Product | HBPS | NaN$_3$ |
|---|---|---|
| 50% HBPS-N3 | 2.00 g | 338 mg |
| 30% HBPS-N3 | 2.00 g | 160 mg |
| 10% HBPS-N3 | 2.00 g | 64 mg |

Figure 4

| Product | HBPS-N$_3$ | Propargyl terminated CTA |
|---|---|---|
| 50% HBPS-CTA | 50% HBPS-N$_3$ (1.16 g) | 2.04 g, 5.20 mmol |
| 30% HBPS-CTA | 30% HBPS-N$_3$ (1.18 g) | 0.965 g, 2.46 mmol |
| 10% HBPS-CTA | 10% HBPS-N$_3$ (1.25 g) | 0.386 g, 0.984 mmol |

Figure 5

| Product | HBPS-CTA | NIPAM |
|---|---|---|
| 50-1 HBPS-PNIPAM | 50% HBPS-CTA (14 mg) | 0.28 g |
| 50-2 HBPS-PNIPAM | 50% HBPS-CTA (28 mg) | 0.28 g |
| 50-3 HBPS-PNIPAM | 50% HBPS-CTA (56 mg) | 0.28 g |
| 30-1 HBPS-PNIPAM | 30% HBPS-CTA (35 mg) | 0.28 g |
| 30-2 HBPS-PNIPAM | 30% HBPS-CTA (71 mg) | 0.28 g |
| 30-3 HBPS-PNIPAM | 30% HBPS-CTA (137 mg) | 0.28 g |
| 10-1 HBPS-PNIPAM | 10% HBPS-CTA (56 mg) | 0.28 g |
| 10-2 HBPS-PNIPAM | 10% HBPS-CTA (140 mg) | 0.28 g |
| 10-3 HBPS-PNIPAM | 10% HBPS-CTA (190 mg) | 0.28 g |

|      | Charged mol. wt | Actual mol. wt. | PDI  | PNIPAM content |
|------|-----------------|-----------------|------|----------------|
| 50-1 | 80,000          | 28,000          | 1.39 | 97 w%          |
| 50-2 | 40,000          | 17,000          | 1.20 | 95 w%          |
| 50-3 | 10,000          | 10,000          | 1.11 | 92 w%          |
| 30-1 | 55,000          | 24,000          | 1.21 | 95 w%          |
| 30-2 | 25,000          | 13,000          | 1.11 | 91 w%          |
| 30-3 | 15,000          | 10,000          | -    | 70 w%          |
| 10-1 | 100,000         | 21,000          | 1.22 | 89 w%          |
| 10-2 | 40,000          | 11,000          | 1.12 | 81 w%          |
| 10-3 | 30,000          | 10,000          | -    | 54 w%          |

Figure 11
(1) As cultured
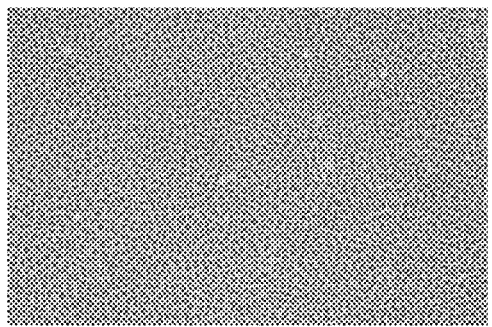
(2) After cooling
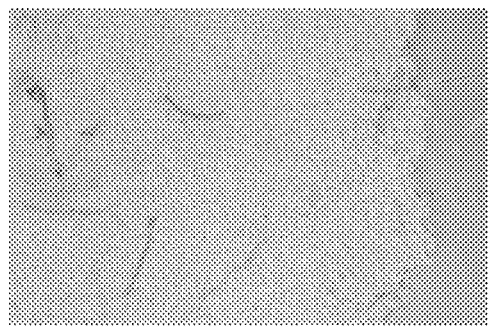
Figure 12
(1) As cultured
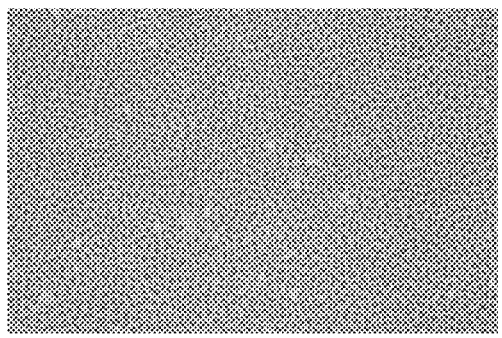
(2) After cooling
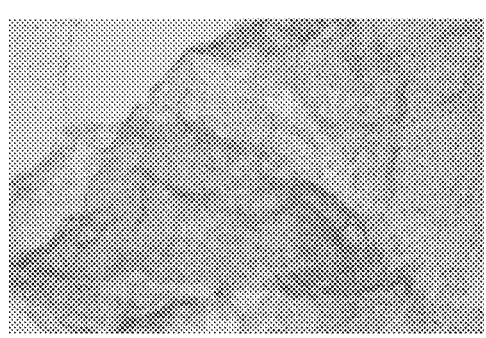
Figure 13
(1) As cultured
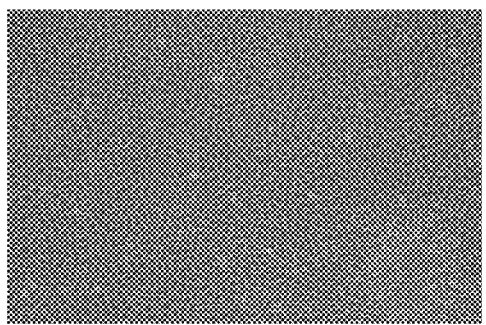
(2) After cooling
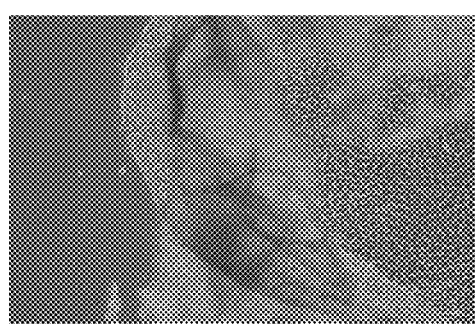

GRAFT POLYMER, TEMPERATURE-RESPONSIVE SUBSTRATE FOR CELL CULTURE USING THE SAME AND PRODUCTION METHOD THEREFOR, AS WELL AS LIQUID CHROMATOGRAPHIC CARRIER HAVING THE NOVEL GRAFT POLYMER IMMOMIBILIZED THEREON AND LIQUID CHROMATOGRAPHIC METHOD USING THE SAME

This application is a continuation of application Ser. No. 16/660,897 filed Oct. 23, 2019, which is a continuation of application Ser. No. 16/208,163 filed Dec. 3, 2018, which is a continuation of application Ser. No. 14/771,068 filed Nov. 30, 2015, which is the U.S. national phase of International Application No. PCT/JP2014/055178 filed Feb. 28, 2014, which designated the U.S. and claims priority to JP Patent Application Nos. 2013-055630 and 2013-055631 filed Feb. 28, 2013, and 2013-189831 filed Aug. 27, 2013, the entire contents of each of which are hereby incorporated by reference.

TECHNICAL FIELD

The present invention relates to a novel graft polymer that is useful in biology, medicine and other fields, as well as a temperature-responsive substrate for cell culture using the polymer and a method for producing the substrate. The present invention also relates to a carrier that can be prepared by a simple method and which is suitable for use in liquid chromatography that is carried out by controlling the interactions on a solid surface to separate valuables such as pharmaceuticals, bio-related substances (e.g. proteins, DNA, and glycolipids) and cells, as well as a method of liquid chromatography using the carrier.

BACKGROUND ART

With recent remarkable advances in the animal cell culturing technology, R&D activities targeting animal cells are spreading in a wider range of fields. The way of using the target animal cells has also changed; in the early stage of development, attempts were made to commercialize animal cells per se or their products, but now, it is becoming possible to design valuable pharmaceuticals by analyzing cells or their outer surface proteins or perform therapies with cells that have been taken out of a patient, then either proliferated in number or enhanced in their functions, and returned into the patient's body. Currently, the techniques of culturing animal cells constitute one area that is attracting the attention of many researchers.

One basic feature of animal cells including human cells is that many of them are adhesion-dependent. In other words, animal cells must be adhered to a certain place before they are cultured ex vivo. Given this background, many researchers have so far designed or invented substrate surfaces that would be more favorable to cells but all proposals have been directed to the phase during cell culture. When cultured adhesion-dependent cells adhere to something else, they will produce adhesive proteins on their own. Hence, in order to exfoliate the cells, the prior art requires disrupting the adhesive proteins and an enzymatic treatment is usually performed. In the process, outer surface proteins that the cells have produced during culture and which are inherent in the respective cells are also disrupted; in spite of its seriousness, no effective means have been available to solve the problem, with no particular studies made. Solving this problem involved in the phase during cell recovery would be a requirement which indeed must be satisfied before dramatic advances can be seen in future R&D activities targeting animal cells.

High performance liquid chromatography (HPLC) has a wide variety of combinations of the mobile-phase liquid and the stationary phase, from which a suitable combination can be selected depending upon the sample; hence, in recent years, HPLC is utilized to separate and purify various substances. However, in the conventionally used chromatography, interactions between the solute in the mobile phase and the surface of the stationary phase are driven not by changing the surface structure of the stationary phase but mainly by changing the solvent in the mobile phase. For example, in HPLC finding use in a lot of areas, normal-phase columns in which a carrier such as silica gel is used as stationary phase employ a mobile phase comprising an organic solvent such as hexane, acetonitrile or chloroform, and reversed-phase columns for separating highly water-soluble substances with a silica gel derivative being used as a carrier employ an organic solvent such as methanol or acetonitrile.

In ion-exchange chromatography which uses an anion exchanger or a cation exchanger as stationary phase, the concentration or type of the external ion is altered to separate substances. With recent rapid advances in genetic engineering and like fields, use of physiologically active peptides, proteins, DNA, etc. is desired in various fields including pharmaceuticals, and their separation and purification is an extremely important issue. In particular, the need for techniques capable of separating and purifying physiologically active substances without impairing their activities is growing.

Unfortunately, however, organic solvents, acids, alkalis and surfactants that are used in the conventional mobile phase not only impair the activity of physiologically active substances, they are also foreign substances, so improvements of the separation and purification system are desired. It is also necessary to avoid the environmental pollution by these substances and this is another reason why a separation and purification system that does not use them is required.

Given this background, various studies have heretofore been made. Patent Document No. 1 discloses a novel cell culture method which comprises providing a cell culture support having a substrate surface coated with a polymer the upper or lower critical solution temperature of which with respect to water is 0-80° C., culturing cells on the support at a temperature either below the upper critical solution temperature or above the lower critical solution temperature, and subsequently adjusting the temperature either to a point equal to or above the upper critical solution temperature or to a point equal to below the lower critical solution temperature, whereby the cultured cells are exfoliated without enzymatic treatment.

Patent Document No. 2 discloses that using this temperature-responsive cell culture substrate, skin cells are cultured at a temperature either below the upper critical solution temperature or above the lower critical solution temperature, and subsequently adjusting the temperature either to a point equal to or above the upper critical solution temperature or to a point equal to below the lower critical solution temperature, whereby the cultured skin cells are exfoliated while suffering low damage.

Patent Document No. 3 discloses a method of repairing outer surface proteins on cultured cells using this temperature-responsive cell culture substrate. By utilizing the temperature-responsive cell culture substrate, it has become possible to modify the conventional culture technology in various novel ways.

By utilizing the temperature-responsive cell culture substrate, it has now become possible to modify the conventional culture technology in various novel ways. However, the technology here mentioned involves coating the surfaces of chemically inactive engineering plastics using high energy radiations such as an electron beam and to this end, expensive equipment such as an electron beam exposure unit is required and this has caused the problem of an inevitable increase in the cost of the culture substrate.

With a view to solving this problem, several techniques have been developed to date. Representative among them are methods of coating a substrate surface with synthesized polymers having the particular molecular structures disclosed in Non-Patent Document Nos. 1 and 2. But neither method is of such a technical level that it is capable of culturing cells in a comparable way to the conventional substrate for cell culture, that it enables the cells to be exfoliated by simply changing the temperature in a comparable way to the above-described temperature-responsive substrate for cell culture which has been prepared using an electron beam, and that the cultured cells are exfoliated as a cell sheet once they have become confluent, and an improvement in their technical level has been required. Considering this point, Patent Document No. 4 discloses that a substrate surface coated with a temperature-responsive polymer joined to a block copolymer would allow cultured cells to be exfoliated in a cell sheet form; as it turned out, however, the substrate was simply coated with a uniform layer of the temperature-responsive polymer and, hence, the ability to exfoliate the cultured cells was limited.

Among the techniques of temperature-responsive chromatography, the one disclosed in Patent Document No. 1 notably provides a platform technology. Described in this document is a technique which comprises providing a cell culture support comprising a substrate surface coated with a polymer the upper or lower critical solution temperature of which with respect to water is 0-80° C., culturing cells on the support at a temperature either below the upper critical solution temperature or above the lower critical solution temperature, and subsequently adjusting the temperature either to a point equal to or above the upper critical solution temperature or to a point equal to below the lower critical solution temperature, whereby the cultured cells are exfoliated. While this was the first case of using the temperature-responsive polymer as a cell culture material in the field of bio-medicine, the fact is that when cells are adhering to the substrate surface, they will secrete adhesive proteins on their own and use the secreted proteins as a linker for adhesion to the substrate surface. Therefore, the phenomenon here contemplated of cells exfoliating from the substrate surface implies that the adhesive proteins secreted from the cells are also exfoliated from the substrate surface. As a matter of fact, when cells obtained by this technique are re-seeded or transplanted into a biological tissue, the cells exfoliated from the substrate will efficiently adhere to the substrate or tissue. This means that the exfoliated cells retain the adhesive proteins as such after they were secreted during culture. In other words, the technique of interest is exactly the concept of the temperature-responsive chromatographic technique as referred to in the present invention which involves eliminating adsorbed proteins through temperature changes.

Patent Document No. 5 made a study about immobilization on silica gel or polymer gel that is commonly used as chromatographic carriers. However, even considering Examples, the document shows no results (as separation charts) of solute separation in the case where those carriers were actually used, and details as to what substances could be separated using these carriers and what was the specific issue to address were unknown.

In Patent Document No. 6, a temperature-responsive polymer was immobilized on the surface of silica gel and cases are shown where various steroids and even lymphocytes were actually separated using the resulting carrier. It is definitely shown that the various steroids and even lymphocytes were actually separated by the characteristics of the temperature-responsive polymer immobilized on the surface of the carrier silica gel. However, considering the exemplary results of separation given in the document, the number of theoretical stages at the separation needs to be increased further and there has been a need to provide an innovative technique that is improved over the prior art so greatly as to solve this problem.

PRIOR ART LITERATURE

Patent Documents

Patent Document No. 1: JP H 02-211865 A
Patent Document No. 2: JP H 05-192138 A
Patent Document No. 3: JP 2008-220354 A
Patent Document No. 4: Japanese Patent Application No. 2010-208506
Patent Document No. 5: JP H 05-133947 A
Patent Document No. 6: JP H 07-318661 A Non-Patent Documents Non-Patent Document No. 1: Soft Matter, 5, 2937-2946 (2009)
Non-Patent Document No. 2: Interface, 4, 1151-1157 (2007)

DISCLOSURE OF THE INVENTION

Problems to be Solved by the Invention

The present invention has been accomplished with the aim of solving the aforementioned problems of the prior art. Briefly, the present invention has as its primary objective providing a novel graft polymer having better cell exfoliating functions based on a concept totally different from the prior art.

Another object of the present invention is to provide a novel temperature-responsive surface having better cell exfoliating functions based on a concept totally different from the prior art and a method of suing this surface.

Yet another object of the present invention is to provide a novel liquid chromatographic carrier prepared on the basis of a concept totally different from the prior art. A further object of the present invention is to provide a liquid chromatographic method using this carrier.

Means for Solving the Problems

In order to solve the aforementioned problems with cell culture, the present inventors performed research and development making studies from various angles and eventually came up with a novel graft polymer. Surprisingly, they found that when cells were cultured on a temperature-responsive substrate for cell culture having a substrate surface coated with a graft polymer comprising a dendritic polymer with a styrene skeleton and a temperature-responsive polymer grafted at a terminal thereof, the cultured cells could be efficiently exfoliated by simply cooling the substrate for a short period of time. From the early stage of their research activities, the present inventors focused on the special stereoregularity and morphology on substrate surface of the graft copolymer in which the dendritic polymer with a styrene skeleton was more compact in structure than the linear styrene and of such a structure that the temperature-responsive polymer was concentrated at a terminal of the dendritic polymer, and they were in great hopes that the substrate for cell culture formed from this graft polymer would have higher performance than the prior art temperature-responsive substrate for cell culture. It was also found that the graft polymer that comprised the dendritic polymer with a styrene skeleton and the temperature-responsive polymer grafted at a terminal thereof and which was applied as a coating to the surface of the substrate of the present invention was insoluble in water and, hence, would neither dissolve out into a culture medium during cell culture nor contaminate the cultured cells during their recovery. It was also found that because of these advantages, the temperature-responsive substrate for cell culture of the present invention can be used over and over again. The present invention has been accomplished on the basis of these findings.

In order to solve the aforementioned problems with chromatographic carriers, the present inventors also performed research and development making studies from various angles. As a result and surprisingly enough, they found that the dendritic polymer with a styrene skeleton could be conveniently immobilized in a thin layer on the surface of a resin-based chromatographic carrier and that when the temperature-responsive polymer was grafted to this dendritic polymer, the carrier's surface displayed such a phenomenon that its chromatographic resolution would abruptly change at a certain temperature. At the early stage of their research activities, the present inventors focused on the stereoregularity of the dendritic polymer and the functional groups occurring at high density on the outside of the molecular chain and speculated that if this dendritic polymer was immobilized on the surface of a chromatographic carrier, the functional groups could be provided at high density on the carrier's surface and that if the above-described temperature-responsive polymer was joined to the dendritic polymer, the product would have higher performance than the prior art temperature-responsive chromatographic carrier. The technique offered by the present invention is totally unexpected from the prior art and if combined with the stereoregularity of the dendritic polymer structure per se, it is expected to evolve to a novel chromatographic system that has never existed in the prior art. The present invention has been accomplished on the basis of these findings.

Thus, the present invention provides a graft polymer as a novel material comprising a dendritic polymer with a styrene skeleton and a temperature-responsive polymer grafted at a terminal thereof.

Further, the present invention provides a temperature-responsive substrate for cell culture that has a substrate surface coated with a graft polymer comprising a dendritic polymer with a styrene skeleton and a temperature-responsive polymer grafted at a terminal thereof. The present invention also provides a method for producing the temperature-responsive substrate for cell culture.

Additionally, the present invention provides a liquid chromatographic carrier on which is immobilized a graft polymer comprising a dendritic polymer with a styrene skeleton and a polymer of different composition grafted at a terminal thereof. The present invention also provides a liquid chromatographic method using the liquid chromatographic carrier.

The present invention is briefly described below.

[1] A novel graft polymer comprising a dendritic polymer with a styrene skeleton and a hydrophilic polymer grafted at a terminal thereof.

[2] The novel graft polymer as recited in [1], which has electric charges at a terminal of the dendritic polymer.

[3] The novel graft polymer as recited in any one of [1] and [2], wherein the hydrophilic polymer is one having temperature response.

[4] The novel graft polymer as recited in [3], wherein the polymer having temperature response comprises any one or more of a poly-N-substituted acrylamide derivative, a poly-N-substituted methacrylamide derivative, a copolymer thereof, polyvinyl methyl ether, and partially acetylated polyvinyl alcohol, or a copolymer thereof with another monomer.

[5] The novel graft polymer as recited in [4], wherein the polymer having temperature response is poly-N-isopropylacrylamide.

[6] The novel graft polymer as recited in [4], wherein the another monomer is a monomer having electric charges and/or a hydrophobic monomer.

[7] The novel graft polymer as recited in any one of [1] and [2], wherein the hydrophilic polymer comprises any one or more of polyacrylamide, poly-N,N-diethylacrylamide, poly-N,N-dimethylacrylamide, acrylate having polyethylene oxide in side chains, and methacrylate having polyethylene oxide in side chains.

[8] The novel graft polymer as recited in any one of [1] and [2], wherein the hydrophilic polymer is a mixture of the polymers as recited in any one of [3] to [7].

[9] A temperature-responsive substrate for cell culture comprising a substrate coated with a dendritic polymer with a styrene skeleton and a temperature-sensitive polymer grafted at a terminal thereof.

[10] The temperature-responsive substrate for cell culture as recited in [8], which has electric charges at a terminal of the dendritic polymer.

[11] The temperature-responsive substrate for cell culture as recited in any one of [9] and [10], wherein the polymer having temperature response comprises any one or more of a poly-N-substituted acrylamide derivative, a poly-N-substituted methacrylamide derivative, a copolymer thereof, polyvinyl methyl ether, and partially acetylated polyvinyl alcohol, or a copolymer thereof with another monomer.

[12] The temperature-responsive substrate for cell culture as recited in any one of [9] to [11], wherein the polymer having temperature response is poly-N-isopropylacrylamide.

[13] The temperature-responsive substrate for cell culture as recited in [11], wherein the another monomer is a monomer having electric charges and/or a hydrophobic monomer.

[14] The temperature-responsive substrate for cell culture as recited in any one of [9] to [13], wherein any one or more of polyacrylamide, poly-N,N-diethylacrylamide, poly-N,N-dimethylacrylamide, acrylate having polyethylene oxide in side chains, and methacrylate having polyethylene oxide in side chains are grafted to part of a terminal of the dendritic polymer with a styrene skeleton.

[15] The temperature-responsive substrate for cell culture as recited in any one of [9] to [14], which has a coating of 1.0 to 7.0 µg/cm² in terms of the temperature-responsive polymer.
[16] The temperature-responsive substrate for cell culture as recited in any one of [9] to [15], wherein the content of the temperature-responsive polymer in the graft polymer ranges from 40 to 99.5 wt %.
[17] The temperature-responsive substrate for cell culture as recited in any one of [9] to [16], wherein the molecular weight of the temperature-responsive polymer in the graft polymer is 5000 or more.
[18] The temperature-responsive substrate for cell culture as recited in any one of [9] to [17], wherein a substrate is in the form of a particle, a filament or a plate either individually or in combination of two or more.
[19] The temperature-responsive substrate for cell culture as recited in any one of [9] to [18], wherein a substrate is composed of polystyrene either alone or combined with another material.
[20] A method for producing a temperature-responsive substrate for cell culture by dissolving or dispersing a graft polymer in an organic solvent, applying a solution of the graft polymer uniformly onto a substrate surface, and drying the same.
[21] The method for producing a temperature-responsive substrate for cell culture as recited in [20], wherein the organic solvent is a liquid mixture of tetrahydrofuran and methanol.
[22] The method for producing a temperature-responsive substrate for cell culture as recited in [21], wherein the mixing ratio of tetrahydrofuran and methanol in the mixed solvent is 1:4.
[23] A liquid chromatographic carrier comprising a carrier surface on which a graft polymer is immobilized, wherein the graft polymer comprises a dendritic polymer with a styrene skeleton and a polymer of a different composition joined to a terminal thereof.
[24] The liquid chromatographic carrier as recited in [23], wherein the polymer grafted to the dendritic polymer with a styrene skeleton comprises a polymer having temperature response, and any one or two of a hydrophilic polymer, and a hydrophobic polymer.
[25] The liquid chromatographic carrier as recited in [24], wherein the polymer having temperature response comprises any one or more of a poly-N-substituted acrylamide derivative, a poly-N-substituted methacrylamide derivative, a copolymer thereof, polyvinyl methyl ether, and partially acetylated polyvinyl alcohol, or a copolymer thereof with another monomer.
[26] The liquid chromatographic carrier as recited in [25], wherein the polymer having temperature response is poly-N-isopropylacrylamide.
[27] The temperature-responsive surface as recited in any one of [25] and [26], wherein the molecular weight of the polymer having temperature response is 5000 or more.
[28] The temperature-responsive surface as recited in any one of [25] to [27], wherein the content of the polymer having temperature response in the graft polymer ranges from 40 to 99.5 wt %.
[29] The liquid chromatographic carrier as recited in [24], wherein the hydrophilic polymer comprises any one or more of polyacrylamide, poly-N,N-diethylacrylamide, poly-N,N-dimethylacrylamide, acrylate having polyethylene oxide in side chains, and methacrylate having polyethylene oxide in side chains.
[30] The liquid chromatographic carrier as recited in any one of [23] to [29] which has electric charges at a terminal of the dendritic polymer.
[31] The liquid chromatographic carrier as recited in any one of [23] to [30] which has electric charges on the polymer grafted to the dendritic polymer with a styrene skeleton.
[32] The liquid chromatographic carrier as recited in any one of [23] to [31], wherein the graft polymer is immobilized on the surface of the carrier at a dose of 1.0 to 7.0 µg/cm².
[33] The liquid chromatographic carrier as recited in any one of [23] to [32], wherein a carrier is composed of polystyrene either alone or combined with another material.
[34] The liquid chromatographic carrier as recited in any one of [23] to [33], wherein the carrier is in the form of a particle, a filament or a plate either individually or in combination of two or more.
[35] A method for producing a liquid chromatographic carrier by dissolving or dispersing a graft polymer in an organic solvent, applying a solution of the polymer uniformly onto a substrate surface, and drying the same.
[36] The method for producing a liquid chromatographic carrier as recited in [35], wherein the organic solvent is a liquid mixture of tetrahydrofuran and methanol.
[37] The method for producing a liquid chromatographic carrier as recited in [36], wherein the mixing ratio of tetrahydrofuran and methanol in the mixed solvent is 1:4.
[38] A liquid chromatographic method using the liquid chromatographic carrier as recited in any one of [23] to [34].
[39] The liquid chromatographic method as recited in [38] which comprises separating a solute under specified temperature conditions.
[40] The liquid chromatographic method as recited in [38] which comprises separating a solute while varying the temperature such that it crosses the level at which the properties of the carrier surface will change.
[41] The liquid chromatographic method as recited in [38], wherein the temperature variation is either in an intermittent or continuous way or in both intermittent and continuous ways.
[42] The liquid chromatographic method as recited in [38] which comprises adsorbing the solute on the liquid chromatographic carrier and subsequently varying the temperature to change the properties of the carrier surface so that the adsorbed solute becomes free.
[43] The liquid chromatographic method as recited in [38] which comprises separating the solute with two or more types of the liquid chromatographic carrier packed in the same column by varying the temperature such that it crosses the level at which the properties of the carrier surface will change.
[44] The liquid chromatographic method as recited in [38] which comprises separating the solute with the liquid chromatographic carrier in a column the inlet and outlet temperatures of which are so set that the temperature level at which the properties of the carrier surface will change is in between said inlet and outlet temperatures and that a temperature gradient is provided within the column from the inlet to the outlet end.
[45] The liquid chromatographic method as recited in any one of [38] to [44], wherein the mobile phase is an aqueous system.
[46] The liquid chromatographic method as recited in any one of [38] to [45] which is for separating pharmaceuticals, metabolites thereof, agrochemicals, peptides or proteins.

Effects Of The Invention

By using substrates coated on their surface with the novel graft polymer to be described herein, cells can be cultured efficiently and, what is more, the cultured cells can be exfoliated efficiently within a short period of time by simply changing the temperature of the substrate surface. And substrates having such functional surface can be conveniently prepared in accordance with the production method of the present invention.

Additionally, a novel separation system is offered by the liquid chromatographic carrier described herein. Given this system, peptides and proteins can be separated over a wide range. And the stereoregularity of the dendritic polymer itself may be utilized to enable solutes to be separated depending on the differences in their molecular structures.

BRIEF DESCRIPTION OF THE DRAWINGS

FIG. 1 is a diagram showing the synthesis pathway of a dendritic polymer with a styrene skeleton in Example 1.

FIG. 2 is a diagram showing the synthesis pathway of a graft polymer comprising the dendritic polymer with a styrene skeleton and a temperature-responsive polymer grafted at a terminal thereof according to Example 1.

FIG. 3 is a table showing the conditions for synthesis of graft polymers each comprising the dendritic polymer with a styrene skeleton and a temperature-responsive polymer grafted at a terminal thereof according to Example 1.

FIG. 4 is a table showing the conditions for synthesis of graft polymers each comprising the dendritic polymer with a styrene skeleton and a temperature-responsive polymer grafted at a terminal thereof according to Example 1.

FIG. 5 is a table showing the conditions for synthesis of graft polymers each comprising the dendritic polymer with a styrene skeleton and a temperature-responsive polymer grafted at a terminal thereof according to Example 1.

FIG. 11 shows in photo the result of culturing cells on a temperature-responsive surface prepared in Example 3.

FIG. 12 shows in photo the result of culturing cells on another temperature-responsive surface prepared in Example 3.

FIG. 13 shows in photo the result of culturing cells on yet another temperature-responsive surface prepared in Example 3.

BEST MODES FOR CARRYING OUT THE INVENTION

Figure 6:
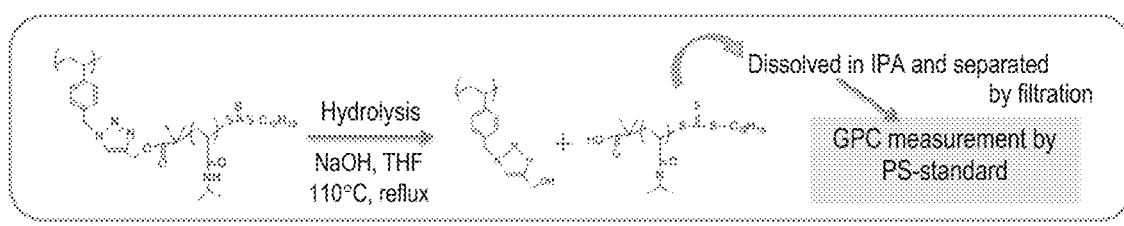
FIG. 6 is a table showing the results of synthesis of graft polymers each comprising the dendritic polymer with a styrene skeleton and a temperature-responsive polymer grafted at a terminal thereof according to Example 1.

The present invention provides a graft polymer comprising a dendritic polymer with a styrene skeleton and a temperature-responsive polymer grafted at a terminal thereof as well as a temperature-responsive substrate for cell culture comprising a substrate surface coated with the graft polymer. The dendritic polymer with a styrene skeleton in the graft polymer coating on the substrate surface will effectively prevent the coating from becoming free from the substrate surface not only during cell culture but also when the cultured cells are exfoliated through temperature change which is the major feature of the present invention. The dendritic polymer as described herein is not particularly limited as long as it has a styrene skeleton. The method of its production also is not particularly limited and it may, for example, be obtained by atom transfer radical polymerization (ATRP) which is commonly performed in chlorobenzene in the presence of copper chloride. In the present invention, in order to extend a temperature-responsive polymer from a terminal of the dendritic polymer with a styrene skeleton, styrene derivatives having functional groups as exemplified by chloromethylstyrene, bromomethylstyrene or other halogenated methylstyrene species need be used either alone or in combinations of two or more species. In that case, the mixing ratio of styrene derivatives having functional groups in all monomers that compose the dendritic polymer typically ranges from 5% (inclusive) to 90% (inclusive), preferably from 10% to 80% (i.e., not less than 10% but not more than 80%), more preferably from 15% to 70% (i.e., not less than 15% but not more than 70%), and most preferably from 20% to 60% (i.e., not less than 20% but not more than 60%). If the mixing ratio of styrene derivatives having functional groups is less than 5%, the efficiency of introducing the temperature-responsive polymer chain from a terminal becomes so low that the percent introduction of temperature-responsive polymer that is desired for the present invention is not attained and the product is not preferred as the graft polymer of the present invention. What is more, the resulting graft polymer is so similar in properties to the polystyrene substrate for its coating that organic solvents that dissolve the graft polymer will also dissolve the substrate surface and no suitable solvents are available for coating the substrate surface with the graft polymer, which is again unfavorable for the purposes of the present invention. On the other hand, if the mixing ratio of styrene derivatives having functional groups is more than 90%, the efficiency of introducing the temperature-responsive polymer chain from a terminal is improved, producing a graft polymer in which the properties of the temperature-responsive polymer predominate; as a result, the graft polymer may become so highly soluble in water that it is likely to dissolve out into the culture medium during cell culture and may even contaminate the cultured cells in the process of recovery; this graft polymer is also unsuitable for use in the present invention. The molecular weight of the dendritic polymer also is not particularly limited but considering its relative proportion with respect to the temperature-responsive polymer to which it is joined, the molecular weight of interest is recommended to range from 2000 to 20000 (i.e., not less than 2000 but not more than 20000), preferably from 2500 to 15000 (i.e., not less than 2500 but not more than 15000), more preferably from 3000 to 10000

(i.e., not less than 3000 but not more than 10000), and most preferably from 4000 to 8000 (i.e., not less than 4000 but not more than 8000). If the molecular weight of the dendritic polymer is smaller than 2000, the relative proportion of the temperature-responsive polymer chain is increased, producing a graft polymer in which the properties of the temperature-responsive polymer predominate; as a result, the graft polymer will become so highly soluble in water that it is likely to dissolve out into the culture medium during cell culture and may even contaminate the cultured cells in the process of recovery, which is not preferred as the graft polymer of the present invention. If, on the other hand, the molecular weight of the dendritic polymer is greater than 20000, the percent introduction of temperature-responsive polymer that is desired for the present invention is not attained and the product is not preferred as the graft polymer of the present invention. What is more, the resulting graft polymer is so similar in properties to the polystyrene substrate for its coating that organic solvents that dissolve the graft polymer will also dissolve the substrate surface and no suitable solvents are available for coating the substrate surface with the graft polymer, which is again unfavorable for the purposes of the present invention. If desired, in the case of the present invention, positive or negative charges as on hydroxyl, carboxyl, amino, carbonyl, aldehyde or sulfonic groups may be added to a terminal of the dendritic polymer in the usual manner; alternatively, positive or negative charges as on hydroxyl, carboxyl, amino, carbonyl, aldehyde or sulfonic groups may be left in the dendritic polymer moiety of the graft polymer as the final form of the compound of the present invention which comprises the dendritic polymer with a styrene skeleton and the temperature-responsive polymer joined to a terminal thereof.

The present invention also provides a liquid chromatographic carrier characterized in that a graft polymer is immobilized wherein the graft polymer comprises a dendritic polymer with a styrene skeleton and a polymer of a different composition joined to a terminal thereof, as well as a liquid chromatographic method using the liquid chromatographic carrier. The present inventors conducted various studies with a view to meeting the above-mentioned demands for liquid chromatographic carriers; as a result, they developed a technique in which separation/purification could be achieved by changing the interactions between the solute and the surface of the stationary phase through a change in an external condition such as temperature on the surface structure of the stationary phase, rather than through a change of the mobile phase. The present invention has been accomplished on the basis of this technique and aims to provide a chromatographic method that involves changing an external condition whereby the surface properties of the stationary phase are changed reversibly so that separation/purification is possible using a single aqueous mobile phase, as well as to provide a packing agent suitable for use as the stationary phase in the chromatographic method. In essence, the present invention provides a chromatographic method characterized by performing solute separation with such a packing agent that if, for example, the graft polymer comprising the dendritic polymer and a temperature-responsive polymer joined thereto is immobilized on a carrier surface serving as the stationary phase, the properties of the surface of the stationary phase will be varied with temperature while the mobile phase is fixed to an aqueous system. The present invention further provides a temperature-responsive chromatographic method using said packing agent. Stated briefly, the use of the present invention enables bio-elements such as peptides, proteins or cells to be separated by bringing the outside temperature to a level equal to or above a critical point. In the process, no chemicals including organic solvents, acids, alkalis, surfactants, etc. are used, so the present invention eliminates the possibility that such chemicals will become foreign substances and can additionally be utilized in separating proteins, cells and other bio-elements in the same manner as they are analyzed with their functions kept intact.

If the conventional chromatographic method is applied, with a single type of mobile phase, to separate and analyze samples containing a variety of compounds in admixture, in particular, a plurality of samples having greatly different polarities, separation is difficult and requires a considerable amount of time to be complete. Therefore, to handle such samples, the amount and type of the organic solvent are changed over time either continuously (solvent gradient method) or in stages (step gradient method). In the temperature gradient method or step gradient method according to the present invention, the same level of separation can be achieved by changing the column temperature either continuously or in stages using a single mobile phase rather than organic solvents. By adopting this approach, contamination by the aforementioned foreign substances can be prevented while ensuring that proteins, cells and other bio-elements can be separated with their functions kept intact and, what is more, the desired components can be separated within a short period of time through temperature-mediated control.

The present invention is described below in a more specific way. The present invention provides a liquid chromatographic carrier on which a graft polymer is immobilized wherein the graft polymer comprises a dendritic polymer with a styrene skeleton and a polymer of a different composition joined to a terminal thereof. And even if only the dendritic polymer is immobilized in a thin layer on the carrier surface, the latter will develop a temperature-responsive property. Although the reason for this phenomenon is not clear as yet, the functions of the dendritic polymer per se presumably changed by a considerable degree as a result of the polymer having been immobilized in a thin layer on the carrier surface, leading to the binding of its molecular chain. In the present invention, factors selected from among the hydrophilicity/hydrophobicity of chromatographic carrier, the degree by which hydrophobic groups in the molecular chain of the dendritic polymer are exposed on the carrier surface, the fluctuation of the molecular chain, the molecule recognizing ability of the molecular chain, exclusion limit, glass transition point, and so forth may have acted either individually or in superposition but it should be understood that this reason will by no means limit the technology of the present invention.

Examples of the temperature-responsive polymer include polymers having a lower critical solution temperature (LCST) and polymers having an upper critical solution temperature (UCST), and these polymers may be homopolymers, copolymers or mixtures thereof. Examples of such polymers include those disclosed in JP H 06-104061 B. Specifically, these may be obtained by homopolymerization or copolymerization of the monomers named below. Applicable monomers include, for example, (meth)acrylamide compounds, N-(or N,N-di)alkyl-substituted (meth)acrylamide derivatives, or vinyl ether derivatives, and partially acetylated polyvinyl alcohol. In the case of copolymers, any two or more of these monomers may be used. In this case, considering that separation is performed at the range of 5° C. to 50° C. since the substances to be separated are biosubstances, exemplary temperature-responsive polymers include poly-N-n-propylacrylamide (21° C. as the lower critical solution temperature of the homopoloymer), poly-N-n-propylmethacrylamide (27° C. as defined above), poly-N-isopropylacrylamide (32° C. as defined above), poly-N-isopropylmethacrylamide (43° C. as defined above), poly-N-cyclopropylacrylamide (45° C. as defined above), poly-N-ethoxyethylacrylamide (ca. 35° C. as defined above), poly-N-ethoxyethylmethacrylamide (ca. 45° C. as defined above), poly-N-tetrahydrofurfurylacrylamide (ca. 28° C. as defined above), poly-N-tetrahydrofurfurylmethacrylamide (ca. 35° C. as defined above), poly-N,N-ethylmethylacrylamide (ca. 56° C. as defined above), poly-N,N-diethylacrylamide (32° C. as defined above), etc. What is more, copolymerization with monomers other than those mentioned above, grafting or copolymerization between polymers, or mixtures of polymers or copolymers may be employed. If desired, polymers may be crosslinked to such an extent that their inherent properties will not be impaired. Monomers that may be used in the process are not particularly limited and exemplary hydrophobic monomers include alkyl acrylates such as n-butyl acrylate and t-butyl acrylate, and alkyl methacrylates such as n-butyl methacrylate, t-butyl methacrylate, and methyl methacrylate. Additionally, exemplary ionic monomers having charge-generating functional groups include the following: building blocks of polymers having an amino group, such as dialkylaminoalkyl (meth)acrylamide, dialkylaminoalkyl (meth)acrylate, aminoalkyl (meth)acrylate, aminostyrene, aminoalkylstyrene, aminoalkyl(meth)acrylamide, alkyloxyalkyltrimethyl ammonioum salt, and 3-acrylamidopropoyltrimethyl ammonium chloride as a (meth)acrylamidealkyltrimethyl ammonium salt; building blocks of polymers having a carboxyl group, such as acrylic acid and methacrylic acid; and building blocks of polymers having a sulfonic group, such as (meth)acrylamidoalkylsulfonic acid; it should, however, be noted that these are not the sole examples that can be used in the present invention.

In the present invention, the dendritic polymer may have another polymer grafted thereto by such a degree that the temperature response desired in the present invention will not be impaired. Applicable polymers are not particularly limited and hydrophilic polymers may be mentioned. The hydrophilic polymers to be used in the present invention may be either homopolymers or copolymers. Examples include, but are not particularly limited to, polyacrylamide, poly-N,N-diethylacrylamide, poly-N,N-dimethylacrylamide, polyethylene oxide, acrylates having polyethylene oxide in side chains, methacrylates having polyethylene oxide in side chains, polyacrylic acid and salts thereof, and hydrous polymers such as poly(hydroxyethyl methacrylate), poly(hydroxyethyl acrylate), polyvinyl alcohol, polyvinylpyrrolidone, cellulose, and carboxymethyl cellulose.

In the present invention, the foregoing procedure yields a graft polymer comprising the dendritic polymer with a styrene skeleton and the temperature-responsive polymer grafted to a terminal thereof. The content of the temperature-responsive polymer in the graft polymer typically ranges from 40.0 to 99.5 wt % (i.e., not less than 40.0 wt % but not more than 99.5 wt %), preferably from 50 to 99 wt % (i.e., not less than 50 wt % but not more than 99 wt %), more preferably from 70 to 98 wt % (i.e., not less than 70 wt % but not more than 98 wt %), and most preferably from 85 to 97 wt % (i.e., not less than 85 wt % but not more than 97 wt %). Below 40.0 wt %, cultured cells on the graft polymer are difficult to exfoliate even if the temperature is changed and the operational efficiency will drop markedly, which is unfavorable for the purposes of the present invention. What is more, as mentioned earlier, the resulting graft polymer is so similar in properties to the polystyrene substrate for coating that organic solvents that dissolve the graft polymer will also dissolve the substrate surface and no suitable solvents are available for coating the substrate surface with the graft polymer, which is again unfavorable for the purposes of the present invention. On the other hand, above 99.5 wt %, the graft polymer of interest will become so highly soluble in water that it is likely to dissolve out into the culture medium during cell culture and may even contaminate the cultured cells in the process of recovery; this graft polymer is also unsuitable for use in the present invention.

While the temperature-responsive polymer which composes the graft polymer in the present invention can be used if its molecular weight is 3000 and more, the recommended molecular weight is at least 5000, preferably at least 10000, more preferably at least 17000, and most preferably at least 20000. If the molecular weight is smaller than 3000, cultured cells on that polymer are difficult to exfoliate even if the temperature is changed and the operational efficiency will drop markedly, which is unfavorable for the purposes of the present invention.

The graft polymer in the present invention is applied as a coating that contains the temperature-sensitive polymer in an amount ranging from 1.0 to 7.0 μg/cm$^2$ (i.e., not less than 1.0 μg/cm$^2$ but not more than 7.0 μg/cm$^2$), preferably from 2.0 to 5.0 μg/cm$^2$ (i.e., not less than 2.0 μg/cm$^2$ but not more than 5.0 μg/cm$^2$), more preferably from 2.5 to 4.5 μg/cm$^2$ (i.e., not less than 2.5 μg/cm$^2$ but not more than 4.5 μg/cm$^2$), and most preferably from 3.0 to 3.5 μg/cm$^2$ (i.e., not less than 3.0 μg/cm$^2$ but not more than 3.5 μg/cm$^2$). If the coating weight is smaller than 1.0 μg/cm$^2$, cultured cells on the graft polymer are difficult to exfoliate even if the temperature is changed and the operational efficiency will drop markedly, which is unfavorable for the purposes of the present invention. On the other hand, if the coating weight is greater than 7.0 μg/cm$^2$, cells will not readily adhere to the coated area, making it difficult to ensure adequate adhesion of the cells; the resulting substrate for cell culture is by no means preferred for use in the present invention.

In the case of the present invention, the graft polymer comprising the dendritic polymer with a styrene skeleton and the temperature-responsive grafted to a terminal thereof needs to be applied to a substrate surface in only the required amount. Since the graft polymer of the present is water-insoluble, it does not need to be washed after the coating step; hence, the amount of the temperature-responsive polymer in the applied graft polymer will directly contribute to the temperature-responsive polymer on the substrate surface. If necessary, the coating weight of the temperature-responsive polymer may be measured in the usual manner as by FT-IR-ATR, elemental analysis or ESCA, and any one of these methods may be employed.

The graft polymer of the present invention is such that the dendritic polymer with a styrene skeleton which is a water-insoluble polymer and the temperature-responsive polymer which has affinity for water are joined together. Therefore, if this graft polymer is coated on a substrate surface and dried, a fine phase-separated structure is anticipated to form on the substrate surface. While the phase-separated structure is not particularly limited in morphology, size, etc., any presence of the phase-separated structure on the substrate surface to which cells are adhering will enable suppression of their degeneration, which is favorable for the purposes of the present invention.

It should also be mentioned that in the case of the present invention, the dithioester-based functional group which is part of the structure of the RAFT agent will remain at a terminal of the resulting polymer. This is a characteristic phenomenon in RAFT polymerization and after the polymerization reaction ends, additional polymerization reaction can be initiated from that terminal. In the process, the dithioester-based functional group present at a terminal of the temperature-responsive polymer is readily replaced by a thiol group by adding a suitable compound such as 2-ethanolamine. This reaction need not be carried out under any special conditions and it is not only convenient but is a rapid reaction that proceeds in a short period of time. As a consequence, one can obtain a polymer chain having the highly reactive thiol group and, hence, the polymer chain can be selectively and efficiently modified at a terminal with functional molecules having functional groups such as a maleimide group or a thio group. Accordingly, the surface of the temperature-responsive substrate for cell culture and the surface of the temperature-responsive liquid chromatographic carrier, both according to the present invention, can be provided with new functional features. In the process, the types of functional groups are not particularly limited and may include, for example, a hydroxyl group, a carboxyl group, an amino group, a carbonyl group, an aldehyde group, and a sulfonic group. If desired, peptides or proteins that will promote cell adhesion may be immobilized at a terminal of the polymer chain. In this connection, the lower critical solution temperature (LCST) of poly-N-isopropylacrylamide is variable depending on the hydrophilicity or hydrophobicity of the terminal functional group, the approach of introducing functional groups at a terminal of the polymer chain as in the present invention has a potential to provide a new technique for controlling the temperature response of the substrate surface from an unconventional viewpoint.

In the present invention, the above-mentioned variety of polymers is immobilized at a terminal of the dendritic polymer having a styrene skeleton and the method of immobilization is not particularly limited. An exemplary method comprises converting the halogen terminal of the above-mentioned halogenated methylstyrene species to an azide form, then modifying the terminal with an initiator (CTA) of reversible addition-fragmentation chain transfer (RAFT) polymerization by click chemistry, and allowing a variety of monomers to grow from the initiator. The initiator used in the process is not particularly limited and examples include 2,2'-azobis(isobutyronitrile), 2,2'-azobis(4-methoxy-2,4-dimethylvaleronitrile) (V-70), and 2,2'-azobis[(2-carboxyethyl)-2-(methylpropionamidine) (V-057). In the present invention, a polymer chain is allowed to grow from this initiator. The RAFT agent that may be used in the process is not particularly limited and examples include benzyl dithiobenzoate, cumyl dithiobenzoate, 2-cyanopropyl dithiobenzoate, 1-phenylethylphenyl dithioacetate, cumylphenyl dithioacetate, benzyl 1-pyrrolecarbodithioate, cumyl 1-pyrrolecarbodithioate, etc.

The solvent to be used during polymerization in the present invention is not particularly limited and preferred examples are benzene, tetrahydrofuran, 1,4-dioxane, dimethylformamide (DMF), etc. A suitable solvent may be selected, also without any particular limitation, as appropriate for the type of the monomer, RAFT agent and polymerization initiator to be used in polymerization reaction. Other factors including the concentrations of initiator and RAFT agent during polymerization, as well as the reaction temperature and time are not particularly limited and may be varied depending on the object. The reaction mixture may be put to a stationary state or stirred.

In the present invention, the thus obtained graft polymer may be dissolved or dispersed in an organic solvent, followed by coating this copolymer uniformly onto a substrate surface. The solvent to be used in the process is not particularly limited as long as it is capable of dissolving or dispersing the block copolymer of interest and examples include N,N-dimethylacrylamide, isopropyl alcohol, or a liquid mixture of acetonitrile and N,N-dimethylformamide. If a plurality of solvents are to be used, their mixing ratio is not particularly limited and the following examples may be given: in the case of tetrahydrofuran/methanol, the recommended ratio is one for tetrahydrofuran vs. four to six for methanol; in the case of dioxane/normal propanol, the recommended ratio is one for dioxane vs. four to six for normal propanol; in the case of toluene/normal butanol, the recommended ratio is one for toluene and four to six for normal butanol; in the case of the acetonitrile/N,N-dimethylformamide liquid mixture, the recommended ratio is five for acetonitrile vs. one for N,N-dimethylformamide, or four for acetonitrile vs. one for N,N-dimethylformamide, or six for acetonitrile vs. one for N,N-dimethylformamide.

In the present invention, the above-described graft polymer solution need be coated uniformly onto a substrate surface. The coating method is not particularly limited and examples include the use of a spin coater and stationary placement of the substrate on a horizontal table. Subsequent removal of the solvent will provide the temperature-responsive substrate for cell culture or temperature-responsive carrier for liquid chromatography according to the present invention. The method of removing the solvent in the process is not particularly limited and examples include: evaporating the solvent slowly over time at room temperature in the atmosphere; evaporating the solvent slowly over time at room temperature in an environment saturated with the solvent; evaporating the solvent under heating; and evaporating the solvent under reduced pressure; to ensure that the finally prepared temperature-responsive substrate for cell culture or temperature-responsive carrier for liquid chromatography will have a clean surface, the first two of the methods described above are recommended and a particularly preferred method is by evaporating the solvent slowly over time at room temperature in an environment saturated with the solvent.

The cell culture substrate to be coated in accordance with the present invention may be formed of any materials including not only those which are commonly employed in cell culture such as glass, modified glass, polystyrene and poly(methyl methacrylate) but also those which can generally be shaped, as exemplified by graft polymers other than those described above, ceramics, and metals. In terms of shape, the substrate is not limited to dishes for cell culture such as petri dish and may assume the form of a plate, fiber or (porous) particle. If desired, it may safely assume the shape of a vessel commonly used in cell culture, etc. (as exemplified by a flask).

The cell to be used on the surface of the temperature-responsive substrate for cell culture which is obtained in the present invention may be of animal origin and the source of its supply and the method of its preparation are not particularly limited. Examples of the cell that may be used in the present invention include cells derived from animals, insects, plants, etc. as well as from bacteria. Notably, animal cells may originate from a variety of sources including, but not particularly limited to, humans, monkeys, dogs, cats, rabbits, rats, nude mice, mice, guinea pigs, pigs, sheep, Chinese hamsters, cattle, marmosets, and African green monkeys. The culture medium to be used in the present invention is not particularly limited as long as it is capable of culturing animal cells and examples include a serum-free medium, a serum-containing medium, etc. These media may be supplemented with differentiation inducing substances such as retinoic acid and ascorbic acid. The seeding density on the substrate surface is not particularly limited and may be determined in the usual manner.

The temperature-responsive substrate for cell culture according to the present invention enables cultured cells to be exfoliated, without enzymatic treatment, by bringing the temperature of the substrate either to a point equal to or above the upper critical solution temperature of the temperature-responsive polymer or to a point equal to or below its lower critical solution temperature. This process may be performed within a culture broth or other isotonic solutions and a suitable way may be selected depending on the object. For the purpose of exfoliating and recovering the cultured cells at a faster rate with a higher efficiency, the substrate may be tapped or rocked or, alternatively, the culture medium may be agitated with a pipette; these and other suitable methods may be used either alone or in combination.

By making use of the temperature-responsive substrate for cell culture which is described herein, cells obtained from various tissues can be cultured efficiently. Use of this culture method enables the cultured cells to be exfoliated efficiently and intact by simply changing the temperature. Such operations have heretofore required time and operator's skill but according to the present invention, this need is eliminated and mass processing of cells is realized. In the present invention, such an improved surface of culture substrate is prepared by utilizing living radical polymerization and it can be designed conveniently and precisely; by subsequently allowing the reaction to be continued on a terminal of the molecular chain, functional groups can be conveniently introduced and this proves extremely advantageous for cell culture.

The carrier to be used in the present invention is not particularly limited if it is one for use in chromatography and polystyrene is recommended since it is capable of efficient immobilization of the dendritic polymer having a styrene skeleton. In this case, the pore diameter is not particularly limited and typically ranges from 50 to 5000 Å (i.e. not less than 50 Å but not more than 5000 Å), preferably from 100 to 1000 Å (i.e., not less than 100 Å but not more than 1000 Å), and more preferably from 120 to 500 Å (i.e., not less than 120 Å but not more than 500 Å). Below 50 Å, the solutes that can be separated are limited to those which have considerably low molecular weights; above 5000 Å, the surface area of the carrier is so small that separation efficiency will become quite low.

In the present invention, the thusly obtained temperature-responsive liquid chromatographic carrier is packed in a column which is then fitted on a conventional liquid chromatographic unit and utilized as a liquid chromatographic system. In the process, separation in accordance with the present invention is affected by the temperature of the carrier packed in the column. In this case, the method of temperature loading on the carrier is not particularly restricted and in one example, the carrier-packed column is entirely or partially mounted on an aluminum block, water bath, air layer, jacket or the like that have been conditioned to a predetermined temperature.

The separation method is not particularly limited and in one example, the carrier-packed column is held at a specified temperature to separate the solute. The carrier to be used in the present invention will undergo temperature-dependent variations in the properties of its surface. Depending on the substance to be separated, successful separation may be achieved by simply setting the temperature at an appropriate, specified point.

In another example of the separation method, the critical temperature at which the properties of the carrier surface will change is preliminarily determined and solute separation is performed by changing the temperature in such a way that it crosses the level of that critical temperature. In this case, temperature changes will suffice for the properties of the carrier surface to change greatly, so depending on the solute, a great difference is expected to occur in the time when a signal appears (i.e. retention time). In the case of the present invention, the most effective way of utilization is by separating the solute in such a way that the temperature crosses the level of the critical point at which the properties of the carrier surface will change greatly. Usually, in the case where only the dendritic polymer is bound to the carrier surface and the solute is a hydrophobic substance such as a pharmaceutical product, the retention time at temperatures lower than the critical point at which the properties of the carrier surface will change greatly is longer than the retention time at temperatures higher than that critical point. Presumably, for the reason already stated above, the properties of the dendritic polymer on the carrier surface may behave as if the surface were hydrophobic on the lower, rather than higher, temperature side.

In the above-described process of temperature changes, the temperature may be changed, starting from the time of starting the solute to flow, either once or two or more times in an intermittent or continuous manner. If desired, these methods may be combined. In this case, temperature may be changed either manually or with the aid of a device capable of programmed automatic temperature control.

Alternatively, another separation method may be performed by making use of the catch-and-release approach, in which the solute is once adsorbed on the prepared temperature-responsive liquid chromatographic carrier and thereafter the adsorbed solute is made free by changing the temperature and, hence, the properties of the carrier surface. In the process, the amount of the solute to be adsorbed may or may not exceed the maximum amount that can be adsorbed on the carrier. In either case, the alternative separation method involves adsorbing the solute once and subsequently making the adsorbed solute free by changing the temperature and, hence, the properties of the carrier surface.

In yet another separation method, two or more temperature-responsive liquid chromatographic carriers are packed within the same column and the solute is separated by changing the temperature in such a way that it crosses the level of the critical point at which the properties of the carrier surface will change. In this case, if the number of carriers used is two, for example, three critical temperature zones occur where the properties of the carrier surface will vary and temperature change may be effected by the above-described method in such a way that the temperature will cross the level of the critical point in each of those zones. If desired, this may be performed with two or more temperature-responsive liquid chromatographic carriers being packed within two or more columns.

In still another separation method, the solute is separated with the temperature-responsive liquid chromatographic carrier in a column the inlet and outlet temperatures of which are so set that the point at which the properties of the carrier surface will change is in between said inlet and outlet temperatures and that the temperature in the column is provided with a temperature gradient from the inlet to the outlet end. The method of changing the temperature stepwise is not particularly limited and examples are by keeping the temperature in the whole column at a predetermined level while securely monitoring the inlet and outlet temperatures of the column or by bringing the column into contact with a plurality of connected aluminum blocks having different temperatures.

As described on the foregoing pages, the present invention enables the solute to be separated by simply changing the temperature while fixing the mobile phase. In the process, the mobile phase is preferably a 100% aqueous system but in the case of the present invention which depends on the properties of the dendritic polymer immobilized on the carrier surface, the composition of the mobile phase is not a particular limiting factor and it may contain a solvent, its pH may be changed, or a salt may be contained in it. In the process, the concentration of the solvent may be changed to perform the solvent gradient method in combination with the use of the carrier of the present invention. If desired, the mobile phase may entirely be composed of an organic solvent.

The temperature-responsive liquid chromatographic carrier and the chromatographic method using the same that have been described above according to the present invention enable separation of pharmaceuticals and their metabolites, as well as agrochemicals, peptides, and proteins. In the process, separation can be accomplished by the simple operation of changing the temperature within the column.

EXAMPLES

On the following pages, the present invention will be described in greater detail by referring to Examples but these are by no means intended to limit the present invention.

Example 1

(1) Synthesis of a Hyperbranched Polystyrene (HBPS)

Figure 7:
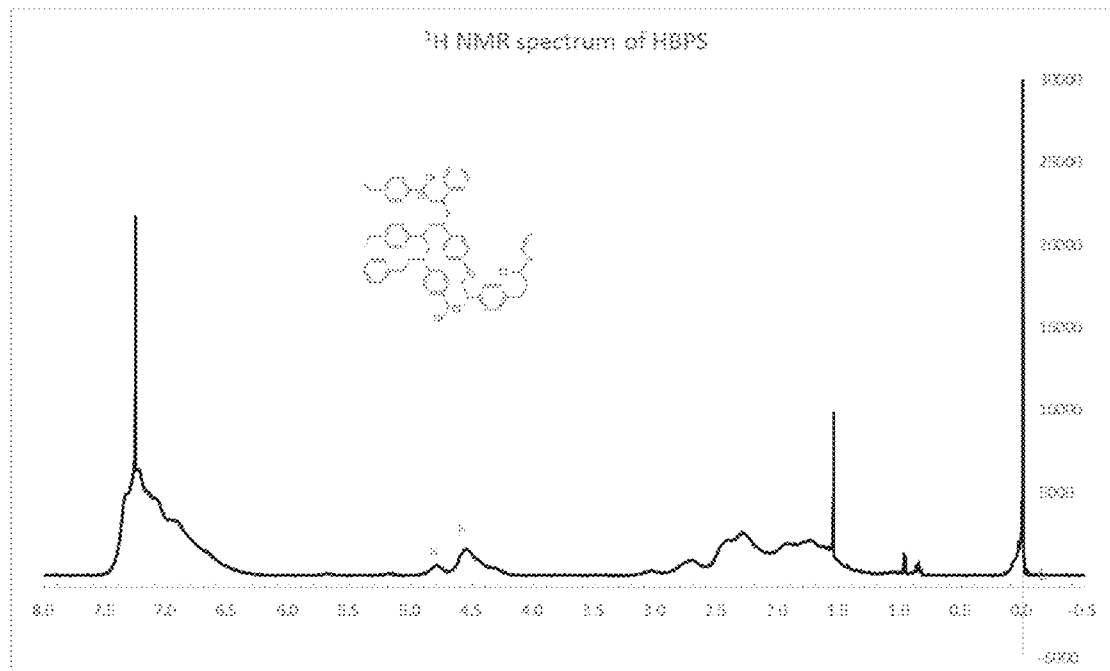
FIG. 7 is a chart depicting the result of synthesizing the dendritic polymer with a styrene skeleton according to Example 1.

A Schlenk flask was charged with styrene (8.05 g), CMS (5.46 g) and chlorobenzene (20 mL) and a freeze-pump-thaw cycle was repeated three times for degasification. Subsequently, 2,2'-bipyridyl (1.64 g) and CuCl (0.520 g) were added, followed by repeating a freeze-pump-thaw cycle three additional times for complete degasification; thereafter, the reaction mixture was stirred under vacuum in an oil bath (120° C.). Four hours later, the reaction was brought to an end by cooling and after about 2-fold dilution with THF, the reaction mixture was passed through neutral alumina to remove the copper catalyst. The reaction mixture was further subjected to re-precipitation with hexane and vacuum-dried overnight at 60° C. to yield a pure polymer (hereinafter referred to as HBPS). The product was analyzed by NMR to give the result shown in FIG. 7, from which one can see that the desired product had been obtained.

(2) Synthesis of RAFT Agent (CTA; Reversible Addition-Fragmentation Chain-Transfer Agent)

An eggplant-shaped flask was charged with tripotassium phosphate (1.02 g), dodecanethiol (1.34 g) and acetone (20 mL) and after stirring the mixture for 10 minutes, carbon disulfide (1.37 g) was added and stirring was continued for an additional 10 minutes. Then, 2-bromoisobutyric acid (1.00 g) was added and, thereafter, the mixture was stirred at room temperature for 13 hours in a nitrogen atmosphere. The solvent in the reaction mixture was distilled off and the residue was dissolved in dichloromethane, followed by extraction of the organic layer by phase separation with 1M hydrochloric acid, water and saturated brine. Further purification by silica gel chromatography gave the desired product as a yellow crystal.

(3) Synthesis of Propargyl Terminated CTA

The above-prepared CTA (1.00 g), propargyl alcohol (0.308 g) and DMAP (0.355 g) were put into an eggplant-shaped flask and purged with nitrogen, followed by addition of dichloromethane (50 mL). After stirring the reaction mixture at 0° C. for 30 minutes, DCC (0.567 g) dissolved in DCM (5 mL) was slowly added dropwise and the resulting mixture was stirred for 24 hours. After the reaction, the by-product was filtered off and the solvent was removed; by subsequent silica gel chromatography, the desired product of a bright, dark orange color was isolated.

(4) Block Copolymerization of PNIPAM at a Terminal of the Hyperbranched Polystyrene (4-1) Converting a Terminal of the Hyperbranched Polystyrene to an Azide Form The above-obtained HBPS and $NaN_3$ (FIG. 3) were purged with nitrogen and, after adding DMF (10 mL), the mixture was stirred at 45° C. for 3 days. After the reaction, DMF was distilled off and the residue was dissolved in DCM, followed by extraction of the organic layer by phase separation with water and saturated brine. The extracted organic layer was vacuum-dried overnight at 45° C. Since the resulting polymer terminated with an azide form (hereinafter referred to as $HBPS-N_3$) was unstable, it was dried and immediately subjected to the following reaction.

(4-2) Modifying a Terminal of the Hyperbranched Polystyrene with CTA (Click Reaction)

An eggplant-shaped flask was charged with the propargyl terminated CTA obtained in step (3) and various grades of $N_3$-HBPS in the amounts indicated in FIG. 4 and, after nitrogen purge together with $Cu(PPh_3)_3Br$ (30 mg), DMF (20 mL) was added. After stirring at room temperature for 3 days, DMF was distilled off. The residue was dissolved in THF and after re-precipitation with hexane, the precipitate was vacuum-dried overnight at 40° C. to isolate the polymer modified with CTA at a terminal (hereinafter referred to as HBPS-CTA).

Figure 8:
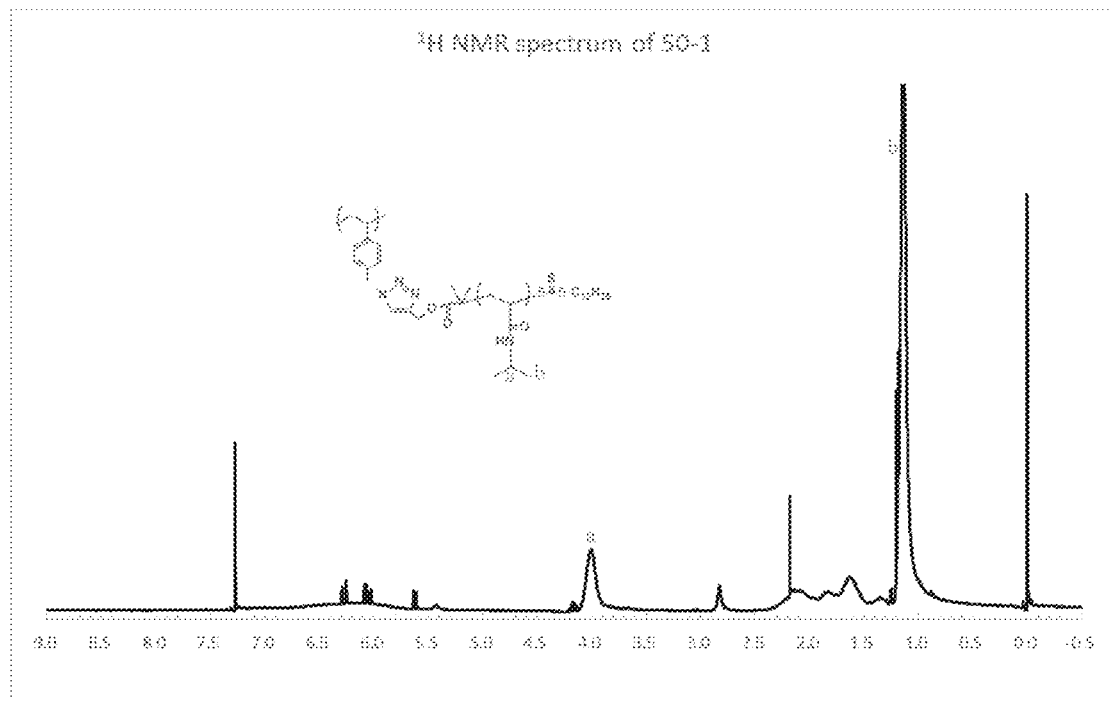
FIG. 8 is a chart depicting the result of synthesizing a graft polymer comprising the dendritic polymer with a styrene skeleton and a temperature-responsive polymer grafted at a terminal thereof according to Example 1.
Figure 9:
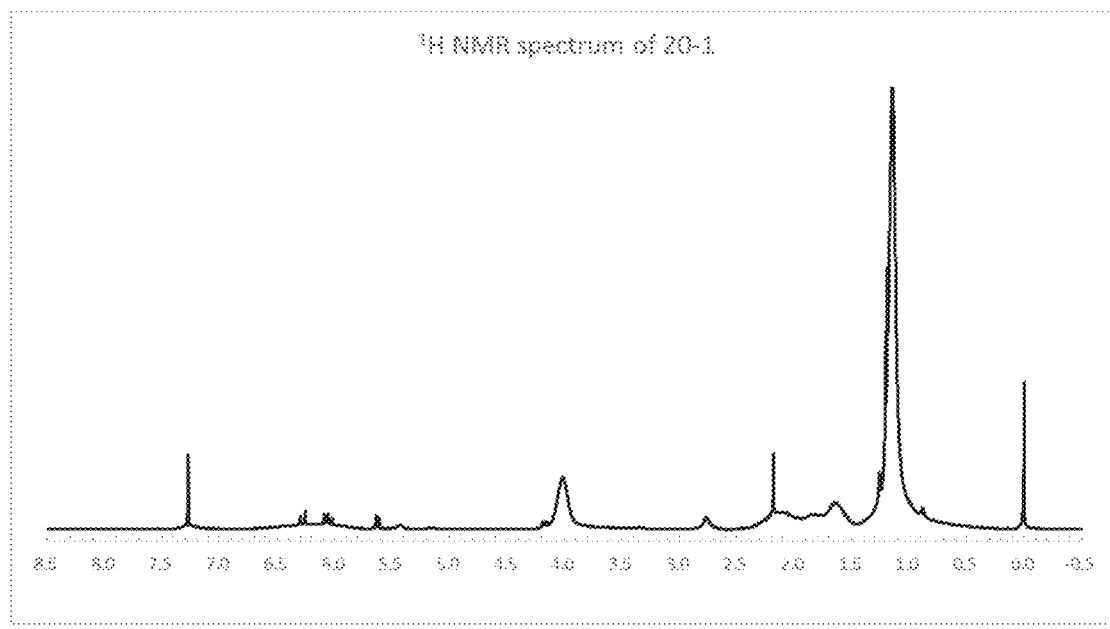
FIG. 9 is a chart depicting the result of synthesizing a graft polymer comprising the dendritic polymer with a styrene skeleton according to Example 1 and a temperature-responsive polymer grafted at a terminal thereof.
Figure 10:
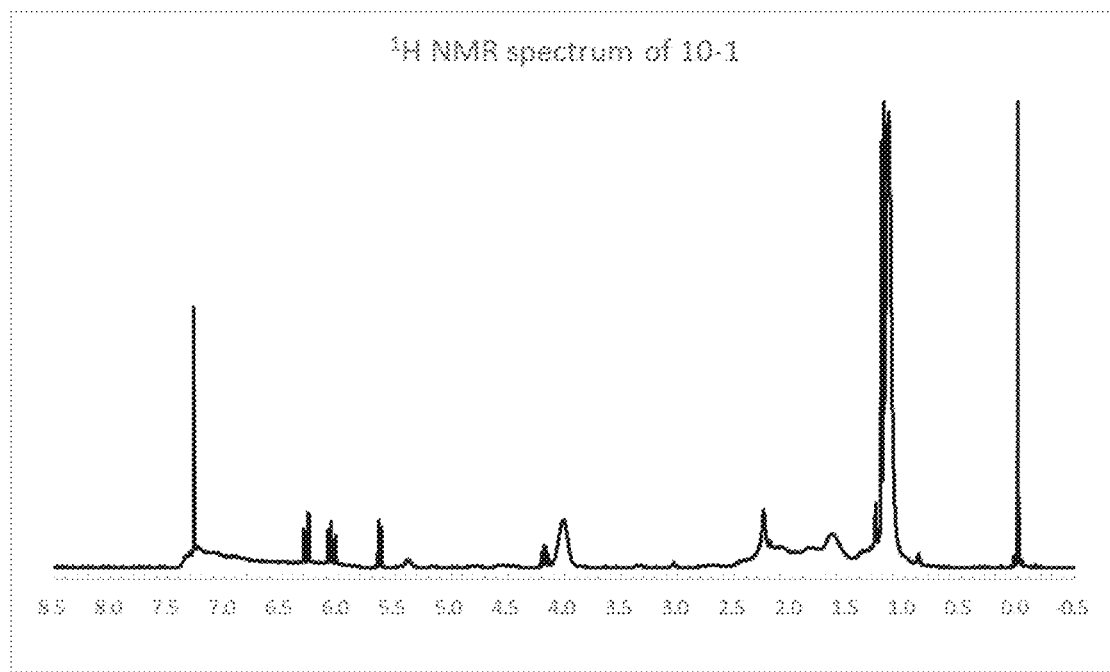
FIG. 10 is a chart depicting the result of synthesizing a graft polymer comprising the dendritic polymer with a styrene skeleton and a temperature-responsive polymer grafted at a terminal thereof according to Example 1.

(4-3) Reversible Addition-Fragmentation Chain-Transfer (RAFT) Polymerization of PNIPAM A 5-mL frozen ampoule was charged with AIBN (1 mg), THF (1.5 mL), NIPAM and various grades of HBPS-CTA in the amounts indicated in FIG. 5. The system was degassed by repeating a freeze-pump-thaw cycle four times and the mixture was stirred at 70° C. for 24 hours under vacuum. After the reaction, the mixture was cooled on an ice bath, followed by dilution with THF and re-precipitation with hexane. The precipitate was vacuum-dried overnight at 45° C. to yield the final product (HBPS-PNIPAM). Samples 50-1, 20-1 and 10-1 were analyzed by NMR to give the results shown in FIGS. 8, 9 and 10, respectively, from which one can see that the desired products had been obtained.

Example 2

Coating HBPS-PNIPAM onto a Cell Culture Substrate Surface (2-1) Preparing HBPS-PNIPAM Coating Solution Approximately 10 mg of each sample of HBPS-PNIPAM was collected in a sample bin and after accurately weighing the sampled quantity, 4 ml of tetrahydrofuran/methanol (mixed at a ratio of 1:4) which would serve as the developing solvent for the coating of HBPS-PNIPAM was added by pipetting to make a solution (hereinafter referred to as the stock solution of polymer.) This stock solution of polymer was divided into predetermined smaller portions which were diluted with predetermined amounts of tetrahydrofuran/methanol (mixed at a ratio of 1:4) to prepare diluted solutions (hereinafter referred to as polymer coating solutions). The respective polymer coating solutions contained HBPS-PNIPAM dissolved in amounts of 57.6 µg, 48.0 µg, 43.2 µg, 38.4 µg, 33.6 µg, 28.8 µg, 24.0 µg, 19.2 µg and 14.4 µg in 50 µl.

(2-2) Coating HBPS-PNIPAM onto a Surface of Cell Culture Substrate

The respective polymer coating solutions obtained in step (2-1) were each added dropwise in a specified amount of 50 µl over a commercial PSt petri dish (product of Becton, Dickinson Company; Falcon 3001 with a culture area of 9.6 cm$^2$). Thereafter, the dishes were lidded and left to stand at room temperature for 90 minutes, during which the solvent consisting of tetrahydrofuran/methanol (mixed at a ratio of 1:4) evaporated slowly to yield PSt petri dishes coated with HBPS-PNIPAM (hereinafter referred to as temperature-responsive petri dishes). Since the polymer coating solutions containing HBPS-PNIPAM dissolved in amounts of 57.6 µg, 48.0 µg, 43.2 µg, 38.4 µg, 33.6 µg, 28.8 µg, 24.0 µg, 19.2 µg and 14.4 µg were each applied in an amount of 50 µl onto the PSt petri dish having a culture area of 9.6 cm$^2$, the PSt petri dishes were coated with HBPS-PNIPAM at respective doses of 6.0 µg/cm$^2$, 5.0 µg/cm$^2$, 4.5 µg/cm$^2$, 4.0 µg/cm$^2$, 3.5 µg/cm$^2$, 3.0 µg/cm$^2$, 2.5 µg/cm$^2$, 2.0 µg/cm$^2$ and, 1.5 µg/cm$^2$.

Example 3

Evaluation of Temperature-Responsive Petri Dishes for Cell Quality

On each of the temperature-responsive petri dishes prepared in Example 2, 3T3 mouse fibroblasts were seeded, and each dishes was evaluated for cell quality by examining the adhesion of cells and by checking for the ability of cultured cells to exfoliate upon cooling, in the early stage of culture (after one day of culture) and after prolonged culture (after four days of culture).

(3-1) Evaluation of Temperature-Responsive Petri Dishes for Cell Quality in the Early Stage of Culture To each of the temperature-responsive petri dishes, 2 ml of a medium (Dulbecco's modified Eagle's medium (DMEM) containing 10% fetal calf serum) was added and after further adding 200 µl of a medium containing 1×10$^5$ 3T3 mouse fibroblasts dispersed therein, culture was conducted in a CO$_2$ incubator (37° C., 5% CO$_2$) for 24 hours. After the end of culture, the cultured cells were observed with an inverted microscope to see how they adhered. Thereafter, the temperature-responsive petri dishes containing the cultured cells were left to stand in a cold CO$_2$ incubator (20° C., 5% CO$_2$) to be cooled for 15 minutes. After the cooling, the cultured cells were observed with an inverted microscope to see how they were exfoliated.

(3-2) Evaluation of Temperature-Responsive Petri Dishes for Cell Quality after Prolonged Culture To each of the temperature-responsive petri dishes, 2 ml of a medium (Dulbecco's modified Eagle's medium (DMEM) containing 10% fetal calf serum) was added and after further adding 200 µl of a medium containing 1×10$^5$ 3T3 mouse fibroblasts dispersed therein, culture was conducted in a CO$_2$ incubator (37° C., 5% CO$_2$) for 4 days. After the end of culture, the cultured cells were observed with an inverted microscope to see how they adhered and whether they had proliferated until confluence in the petri dishes. Thereafter, the temperature-responsive petri dishes containing the cultured cells were left to stand in a cold CO$_2$ incubator (20° C., 5% CO$_2$) to be cooled for 15 minutes. After the cooling, the cultured cells were observed with an inverted microscope to see whether they were exfoliated in a sheet form. Cells on the petri dish coated with 3.0 µg/cm$^2$ of sample 50-1 appeared as shown in FIG. 11(1) at the end of culture; the cultured cells appeared as shown in FIG. 11(2) after 15-min cooling; cells on the petri dish coated with 3.5 µg/cm$^2$ of sample 50-2 appeared as shown in FIG. 12(1) at the end of culture; the cultured cells appeared as shown in FIG. 12(2) after 15-min cooling; cells on the petri dish coated with 2.5 µg/cm$^2$ of sample 30-1 appeared as shown in FIG. 13(1) at the end of culture; the cultured cells appeared as shown in FIG. 13(2) after 15-min cooling. The results show that when cultured on each sample of the temperature-responsive substrate for cell culture according to the present invention, cells proliferated until they became confluent and that the cultured cells could be exfoliated in a sheet form simply upon cooling for 15 minutes.

Comparative Example 1

Cells were cultured by the same procedure as in Example 3, except that the cell culture substrate was a commercial product without a coating of the temperature-responsive polymer, and an attempt was made to exfoliate the cultured cells by simply cooling the substrate. As it turned out, the cultured cells could not be exfoliated from the commercial culture substrate.

Comparative Example 2

In the process of preparing sample 50-1 in step (4-3) of Example 1, the reaction time was changed to 6 hours, yielding a product with PNIPAM having a molecular weight of 1800. A temperature-responsive culture substrate was prepared by coating 3.5 µg/cm$^2$ of this product in the same manner as in Example 2. On this temperature-responsive culture substrate, cells were cultured by the same procedure as in Example 3 and an attempt was made to exfoliate the cultured cells by simply cooling the substrate. As it turned out, the cultured cells could not be exfoliated from the commercial substrate.

Comparative Example 3

A temperature-responsive substrate was prepared by the same procedure as in Example 2, except that when sample 50-1 was coated onto a substrate surface in accordance with the method of Example 2, the coating weight was changed to 7.5 µg/cm$^2$. An attempt was made to culture cells on the prepared temperature-responsive culture substrate by the same procedure as in Example 3. As it turned out, the cultured cells could not be adhered to the culture substrate used.

Example 4

In step (4-2) of Example 1, the azide group at a terminal of the hyperbranched polystyrene was reacted with acrylic acid to prepare a product in which part of the terminal was converted to a carboxyl group and by subsequently repeating step (4-3) of Example 1 and the procedure of Example 2, there was obtained a temperature-responsive culture substrate that had a coating of sample 50-2 in an amount of 3.5 µg/cm$^2$. On this temperature-responsive culture substrate, cells were cultured by the same procedure as in Example 3 and an attempt was made to exfoliate the cultured cells by simply cooling the substrate. As it turned out, the cells had better adhesion in the early stage of culture and proliferated to a confluent state; the cultured cells were exfoliated in a sheet form by simply cooling the substrate for 15 minutes.

Example 5

On a temperature-responsive culture substrate with a 3.5 µg/cm² coating of sample 50-2 that had been obtained in accordance with the method of Example 2, a single layer of epidermal keratinocytes was cultured in a commercial KGM medium under a serum-free condition by the same procedure as in Example 3 and after 14 days of culture, an attempt was made to exfoliate the cultured cells by simply cooling the substrate. As it turned out, the cells had proliferated to a confluent state and the cultured cells were exfoliated in a sheet form by simply cooling the substrate for 15 minutes.

Example 6

On a temperature-responsive culture substrate with a 4.0 µg/cm² coating of sample 50-1 that had been obtained in accordance with the method of Example 2, a single layer of retinal pigment epithelial cells was cultured in a commercial RtEBM medium in the presence of a serum by the same procedure as in Example 3 and after 21 days of culture, an attempt was made to exfoliate the cultured cells by simply cooling the substrate. As it turned out, the cells had proliferated to a confluent state and the cultured cells were exfoliated in a sheet form by simply cooling the substrate for 15 minutes.

Example 7

Coating HBPS-PNIPAM onto a Liquid Chromatographic Carrier Surface
(7-1) Preparing HBPS-PNIPAM Coating Solution
Approximately 10 mg of each sample of HBPS-PNIPAM was collected in a sample bin and after accurately weighing the sampled quantity, 4 ml of tetrahydrofuran/methanol (mixed at a ratio of 1:4) which would serve as the developing solvent for the coating of HBPS-PNIPAM was added by pipetting to make a solution (hereinafter referred to as the stock solution of polymer.) This stock solution of polymer was divided into predetermined smaller portions which were diluted with predetermined amounts of tetrahydrofuran/methanol (mixed at a ratio of 1:4) to prepare diluted solutions (hereinafter referred to as polymer coating solutions.) The respective polymer coating solutions contained HBPS-PNIPAM dissolved in amounts of 57.6 µg, 48.0 µg, 43.2 µg, 38.4 µg, 33.6 µg, 28.8 µg, 24.0 µg, 19.2 µg and 14.4 µg in 50 µl.
(7-2) Coating HBPS-PNIPAM onto a Liquid Chromatographic Carrier Surface
The respective polymer coating solutions obtained in step (7-1) were each added dropwise in a specified amount of 50 µl over commercial PSt beads for liquid chromatography that had been preliminarily placed on a petri dish. Thereafter, the beads were left to stand at room temperature for 90 minutes, during which the solvent consisting of tetrahydrofuran/methanol (mixed at a ratio of 1:4) evaporated slowly to yield liquid chromatographic carriers coated with HBPS-PNIPAM.

Example 8

Separation of Steroids
Two kinds of steroid were dissolved in purified water to prepare 10 ml of a solution containing the steroids in admixture at the concentrations indicated below. The prepared solution of mixed steroids was passed through a PTFE filter (0.2 µm).
Sample A

| 1. Hydrocortisone | 0.03 mg/ml |
| 2. Testosterone | 0.02 mg/ml |

Figure 14:
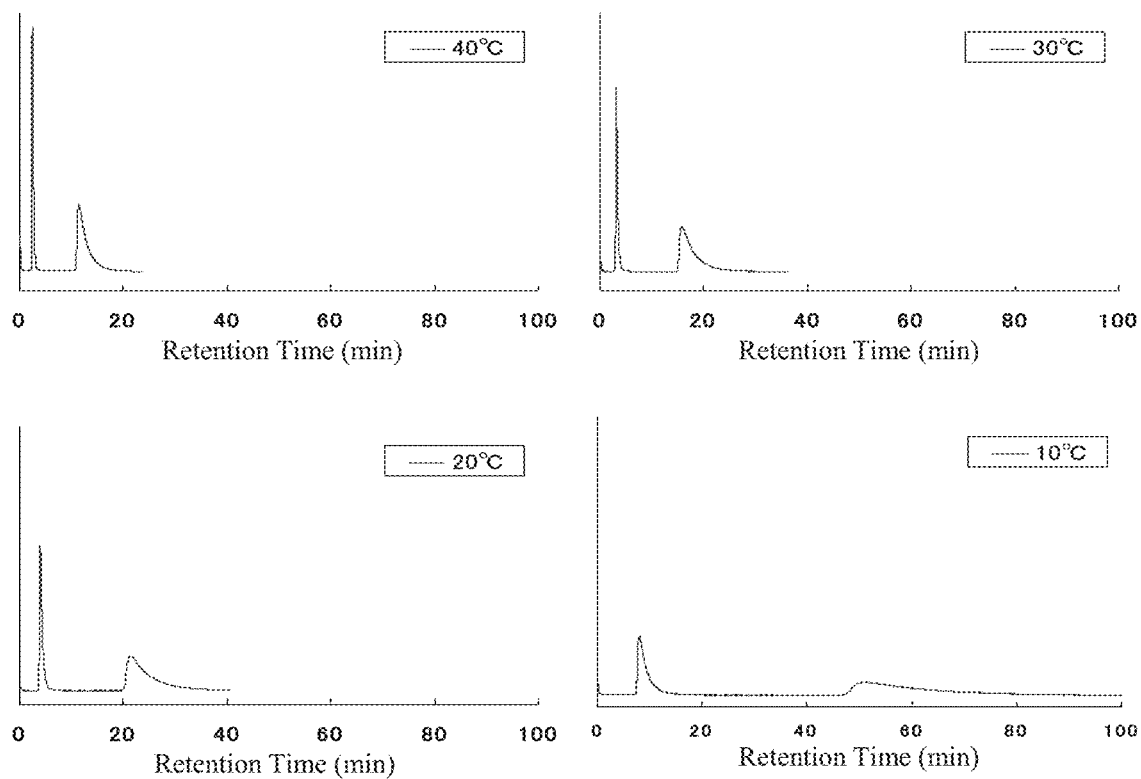
FIG. 14 is a set of charts depicting the results of steroid separation in Example 5.

A column packed with the above-described packing agent (i.e., the temperature-sensitive carrier of the present invention) was loaded with 20 µl of sample A. The column was connected to an HPLC unit, where high-performance liquid chromatography was conducted with a 66.7 mM phosphate buffer as a mobile phase at a flow rate of 1 ml/min and detection was performed with UV from an ultraviolet/visible light absorbance detector at a wavelength of 254 nm. The column was installed in a thermostatic chamber and resolution was compared at varying column temperatures. The results are shown in FIG. 14. At 40° C., testosterone (the right-hand peak in FIG. 14) showed a retention time of 11.5 minutes; at 30° C., the retention time was 15.6 minutes; at 20° C., 21.2 minutes; and at 10° C., 50.9 minutes. Thus, it was verified that changing the column temperature made it possible to vary the hydrophobic interactions at the carrier surface, hence, the retention time of each steroid.

INDUSTRIAL APPLICABILITY

A novel graft polymer can be obtained according to the present invention. If this graft polymer is applied to the temperature-responsive substrate for cell culture described herein, cells obtained from a variety of tissues can be cultured with high efficiency. If this culture method is utilized, cultured cells can be exfoliated intact in a short amount of time with high efficiency.

In addition, by using the chromatographic carrier described herein, a wide range of peptides and proteins can also be separated by simply changing the temperature of the chromatographic carrier. This allows for convenient separation procedure and improves the efficiency of separating operations. What is more, the stereoregularity of the dendritic polymer per se may be utilized to enable separation of solutes based on differences in their molecular structures. The separation procedure attainable by this method is highly likely to be applicable in the development of pharmaceuticals, for example.

Consequently, the present invention will prove extremely useful in a variety of fields including medicine and biology.

The invention claimed is:
1. A temperature-responsive substrate for cell culture comprising a substrate coated with a dendritic polymer with a styrene skeleton and a temperature-sensitive polymer grafted at a terminal thereof,
wherein the dendritic polymer is prepared by using styrene derivatives having functional group in amount of from 5 to 90% based on all monomers that compose the dendritic polymer wherein the functional groups are capable of extending the temperature-responsive polymer from a terminal of the dendritic polymer with styrene skeleton,
wherein the temperature-responsive substrate has a coating of 1.0 to 7.0 µg/cm² in terms of the temperature-responsive polymer, and
the content of the temperature-responsive polymer in the graft polymer ranges from 40 to 99.5 wt %.

2. The temperature-responsive substrate for cell culture according to claim 1, which has electric charges at a terminal of the dendritic polymer.

3. The temperature-responsive substrate for cell culture according to claim 1, wherein the polymer having temperature response comprises any one or more of a poly-N-substituted acrylamide derivative, a poly-N-substituted methacrylamide derivative, a copolymer thereof, polyvinyl methyl ether, and partially acetylated polyvinyl alcohol, or a copolymer thereof with another monomer.

4. The temperature-responsive substrate for cell culture according to claim 1, wherein the polymer having temperature response is poly-N-isopropylacrylamide.

5. The temperature-responsive substrate for cell culture according to claim 1, wherein the another monomer is a monomer having electric charges and/or a hydrophobic monomer.

6. The temperature-responsive substrate for cell culture according to claim 1, wherein any one or more of polyacrylamide, poly-N,N-diethylacrylamide, poly-N,N-dimethylacrylamide, acrylate having polyethylene oxide in side chains, and methacrylate having polyethylene oxide in side chains are grafted to part of a terminal of the dendritic polymer with a styrene skeleton.

* * * * *